(12) United States Patent
Anderson et al.

(10) Patent No.: US 7,198,807 B2
(45) Date of Patent: Apr. 3, 2007

(54) **INHIBITION OF *P. ACNES* USING BOTANICAL EXTRACTS**

(75) Inventors: Mark L. Anderson, Carmel, NY (US); Andres Menendez, Fairview, NJ (US); Rodger E. Bogardus, Basking Ridge, NJ (US)

(73) Assignee: Triarco Industries, Inc., Wayne, NJ (US)

( * ) Notice: Subject to any disclaimer, the term of this patent is extended or adjusted under 35 U.S.C. 154(b) by 0 days.

(21) Appl. No.: 10/726,299

(22) Filed: Dec. 1, 2003

(65) Prior Publication Data

US 2005/0118215 A1 Jun. 2, 2005

(51) Int. Cl.
*A61K 36/00* (2006.01)

(52) U.S. Cl. ..................... 424/729; 424/766
(58) Field of Classification Search ............... 424/729, 424/766
See application file for complete search history.

(56) References Cited

U.S. PATENT DOCUMENTS

| | | | |
|---|---|---|---|
| 4,486,448 A | 12/1984 | Ser et al. .................. 424/294 |
| 4,548,942 A | 10/1985 | Shroot et al. ............... 514/301 |
| 5,411,742 A | 5/1995 | Sebag et al. ................ 424/450 |
| 5,962,517 A | 10/1999 | Murad ........................ 514/474 |
| 6,150,403 A | 11/2000 | Biedermann et al. ....... 514/460 |
| 6,296,880 B1 * | 10/2001 | Murad ........................ 424/616 |
| 6,440,994 B1 | 8/2002 | Sanders, Jr. ................ 514/311 |
| 2003/0165589 A1 * | 9/2003 | Cals-Grieson .............. 424/766 |

FOREIGN PATENT DOCUMENTS

| | | |
|---|---|---|
| FR | WO 01/82887 A1 * | 11/2001 |
| JP | 408092028 A * | 4/1996 |
| KR | 2003073441 A * | 9/2003 |

OTHER PUBLICATIONS

Retrieved from Internet website—Huddleston (2000) "Green Tea: Nature's Rediscovered Ancient Medicine" (3 pages total).*

\* cited by examiner

*Primary Examiner*—Christopher Tate
*Assistant Examiner*—S. B. McCormick-Ewoldt
(74) *Attorney, Agent, or Firm*—Fitzpatrick, Cella, Harper & Scinto

(57) ABSTRACT

Compositions for the treatment of acne have an active ingredient in an amount sufficient to inhibit the growth of *Propionibacterium acnes* and, optionally, at least one inactive ingredient, where the active ingredient is selected from the group consisting of green tea extract, grape seed extract, cranberry extract, and mixtures thereof. The compositions may be substantially free of skin-irritating materials.

2 Claims, No Drawings

INHIBITION OF P. ACNES USING BOTANICAL EXTRACTS

BACKGROUND OF THE INVENTION

1. Field of the Invention

The present invention is related to treatments for acne. In particular, the present invention is directed to compositions and methods for treating acne by inhibiting the growth of *Propionibacterium acnes* bacteria.

2. Related Background Art

Skin disorders are often both irritating and embarrassing. The primary skin disease associated with sebaceous follicles, acne vulgaris ("acne"), is the most common problem treated by dermatologists in the United States. Although there are many treatments, there is no true cure for acne. Treatments include antibiotics that inhibit growth of *Propionibacterium acnes* (*P. acnes*), a bacterium that plays a role in acne; retinoids, such as isotetinoin, sold and prescribed as Accutane®, which reduces sebaceous gland output of sebum, an oily fluid; and antimicrobials, such as benzoyl peroxide. The lesions associated with acne are the result of the rupture of a sebaceous follicle. When the rupture is followed by inflammation and pus, the lesion is known as a "whitehead," and when the rupture is followed by the accumulation of plugged material in the sebaceous follicle, the lesion is known as a "blackhead." This pathophysiology requires both plugging of the upper portion of the follicle, and an increase in sebum production. The upper portion of the follicle, i.e., the pore or infundibulum, into which sebum is secreted, is in direct communication with the skin surface, and may be plugged by cells, sebum, bacteria, and other debris. However, the plugged sebaceous gland continues to produce sebum, stretching the infundibulum until the pore or a lower portion of the follicles ruptures.

Generally, only a minority of sebaceous hair follicles on the face and upper back develop acne lesions. Therefore, it is likely that some structural differentiation predisposes a fraction of the follicles to develop acne. In most males, acne is worst in the teenage years and then subsides, suggesting that a subpopulation of follicles may be present that ultimately self-destruct. In women, teenage acne is often followed by menstrual acne, which flares well into adulthood.

U.S. Pat. No. 6,440,994 to Sanders, Jr., discloses a method of treating inflammatory skin diseases and/or hair loss, comprising administering a therapeutically effective amount of a leukotriene receptor antagonist, an antihistamine, or other anti-inflammatory drug to a patient in need of such treatment. As reported in that patent, acne is a dermatological disorder that affects 17 million Americans with a prevalence rate exceeding 85 percent in teenagers, declining to about 8 percent in 25 to 34 year olds, and 3 percent in 35 to 44 year olds. A number of factors are involved in the condition, its course varies from individual to individual with cause and age, and its response to treatment is often inconsistent.

Sanders, Jr., discloses that, although effective treatments are available for short and long term management of acne, relapses are not uncommon, and, thus, oversight and individualization of the treatment are required. In addition, satisfactory results are not guaranteed with the use of any one of the currently available drugs alone. The medical causes of acne are not fully understood, but the acne of most patients can be managed with a variety of drugs that have been developed recently. However, results vary based on the particular treatment and/or method of medical management. Of the many effective pharmaceutical preparations, both prescription and nonprescription, that are currently available for use in the treatment of acne, relatively few, if any, are free of significant side effects, often causing significant skin irritation. Topical antibiotics decrease the number of mild to moderate inflammatory lesions by inhibiting the growth of *P. acnes*, but are associated with skin irritation, dryness, and potential antibiotic resistance. Oral antibiotics are the standard for treating moderate to severe acne lesions. However, long-term use requires routine laboratory monitoring. Oral vitamin A derivatives, although very effective, are only approved for severe cases, and administration can result in serious side effects and adverse reactions.

Acne appears to be more inflammatory than infectious, inflaming only that portion of the skin near and around the sebaceous gland, and only infecting a single gland. Acne is not characterized by classic cellulitis that would typically migrate from the region of the micro-abscess, but, instead, develops an inflammatory reaction around the lesion that persists. If acne was a truly infectious disease, it would be expected to spread to surrounding tissue if left untreated, creating a substantial problem. However, this rarely, if ever, occurs.

The currently available treatments and management of acne and other inflammatory skin diseases using antibiotics appear to violate basic medical principles. Acne is a characterized as a microabscess. An abscess is typically treated by incision and drainage, not by antibiotics. *P. acnes* is an anaerobic diptheroid organism that does not appear to cause disease in any other areas of the human body, and, thus, is typically not a primary pathogen, but, rather, is as an opportunist that becomes entrapped in a plugged sebaceous gland. This entrapment creates an anaerobic environment, allowing the bacteria to grow and multiply, forming a pustule, and eventually causing an inflammatory response in the skin. In some cases, antibiotic treatment has been useful in inhibiting the growth of the bacteria, which, at least in part, accounts for the limited success seen in patients treated with antibiotics.

U.S. Pat. No. 4,486,448 to Ser, et al., discloses anti-acne compositions containing copper lanolate as the active ingredient. The composition may be in the form of a water-in-oil or oil-in-water emulsion, where the disclosed oils are animal oils, i.e., horse oil, hog oil, and lanolin; vegetable oils, i.e., sweet almond oil, avocado oil, ricin oil, olive oil, grape seed oil, poppy oil, colza oil, peanut oil, corn oil, hazelnut oil, jojoba oil, safflower oil, and wheat germ oil; hydrocarbon oils, i.e., paraffin oil, Purcellin oil, perhydrosqualene and solutions of microcrystalline wax in oils, mineral oils, and oil soluble silicone oils. There is no disclosure or suggestion that the oils, alone, may be used as a treatment for acne.

U.S. Pat. No. 4,548,942 to Shroot, et al., discloses anti-acne compositions comprising derivatives of (5,4b)-isothiazolo pyridine-3-one as an active component. The compositions may be in the form of a cream or as a water-in-oil or oil-in-water emulsion, where the oil may be any of those disclosed by Ser, et al. To reinforce anti-acne activity, the disclosed compositions may also contain antibiotics or macrolids.

U.S. Pat. No. 5,411,742 to Sebag, et al., discloses an acne treatment composition containing a dispersion of ionic or non-ionic amphiphilic lipid vesicles in which the lipid phase contains at least one salicylic acid derivative. The salicylic acid derivatives have an anti-acne activity, and n-dodecanylsalicylates are disclosed as being preferred. The aqueous dispersion of the disclosed compositions may also may contain a dispersion of droplets of a water-immiscible liquid, stabilized by the vesicles, that functions as a carrier for formulation additives. However, there is no disclosure that the water-immiscible liquid acts as a treatment for acne on its own. The disclosed water-immiscible liquids are chosen from the group consisting of: animal and vegetable oils consisting of esters of fatty acid and polyols; the liquid triglycerides sunflower, maize, soya bean, cucurbit, grape seed, jojoba, sesame, hazelnut, and fish oils; glycerol tricaprocaprylate; and vegetable and animal oils of the formula $R_{15}COOR_{16}$, where $R_{15}$ is a higher fatty acid residue containing 7 to 19 carbon atoms, and $R_{16}$ is a branched hydrocarbon chain containing 3 to 20 carbon atoms; the natural and synthetic essential oils eucalyptus, lavandin, lavender, vetiver, litsea cubeba, lemon, sandalwood, rosemary, camomile, savory, nutmeg, cinnamon, hyssop, caraway, orange, geraniol and cade oils; the hydrocarbons hexadecane and paraffin oil; the fluorinated and other halogenated hydrocarbons perfluorotributylamine, perfluorodecahydronaphthalene, fluoroesters and fluoethers; the silicones polysiloxanes, polydimethylsiloxanes and fluorosilicones; esters of inorganic acids and an alcohol; and ethers and polyethers.

U.S. Pat. No. 5,962,517 to Murad discloses orally administered pharmaceutical compositions and methods for treating acne, where the compositions are administered orally. The oral compositions contain an acne reduction component in an amount sufficient to reduce redness and blemishes and a skin conditioning component in an amount sufficient to regulate keratin and sebum production. The acne reduction component contains a vitamin A source, a carotenoid, a vitamin $B_6$ source, and a zinc component. The skin cell conditioning component contains a complex of a transition metal and an organic compound. The disclosed compositions may also contain any of burdock root, yellow dock root, horsetail extract, a catechin-based composition, and a source of any of vitamins $B_1$, $B_2$, $B_3$, $B_5$, C, and E in an amount sufficient to facilitate maintenance of skin cells, as well as at least one amino acid, a magnesium component, a selenium component, and biotin in an amount sufficient to facilitate repair of acne-damaged skin. The catechin-based composition is used as an antioxidant to scavenge free radicals, preventing skin damage, and, preferably, is a proanthanol or proanthocyanidin, such as grape seed extract. There is no disclosure or suggestion that the disclosed oral compositions may be used topically, or that catechin-based compositions alone may be used as a topical treatment for acne.

U.S. Pat. No. 6,150,403 to Biedermann, et al., discloses a method of inhibiting sebaceous gland activity in mammalian skin and scalp by administering a topical composition containing at least one of dehydroacetic acid and its pharmaceutically-acceptable salts, derivatives, and tautomers with a dermatologically-acceptable carrier to the skin or scalp of a mammal susceptible to having excessive sebaceous gland activity.

Typical treatments for acne can cause irritation, dryness, and antibiotic resistance. Therefore, a need exists for a treatment that is effective against acne, but is free of significant side effects. The present invention provides such a treatment.

SUMMARY OF THE INVENTION

The present invention is directed to topical compositions for the treatment of acne that are preferably non-irritating and to methods of treating acne with the compositions of the invention. The compositions of the invention comprise at least one active ingredient in an amount sufficient to inhibit the growth of *P. acnes* and, optionally, at least one inactive ingredient, where the active ingredient is selected from the group consisting of green tea extract, grape seed extract, cranberry extract, and mixtures thereof. The grape seed and green tea extracts are preferably in the form of a dry powder, and the cranberry extract is in the form of a concentrated juice. Preferably, the compositions of the invention are also substantially free of skin-irritating materials.

Preferably, the inactive ingredient, which may act as a carrier, comprises at least one of a water soluble carrier, a petroleum derived carrier, a fatty acid derived or modified carrier, a surfactant, a thickening agent, a carbomer, a polyacrylate, and a silica. Useful water soluble carriers include, but are not limited to, water, alcohols, glycols, glycerin, glycerols, silicones, and cyclic, organic, and polymeric water soluble carriers know in the art. Useful a petroleum derived carriers include, but are not limited to, petroleum, mineral oil, and microcrystalline waxes. Useful fatty acid derived or modified carriers include, but are not limited to, fatty alcohols, stearic acid, stearates, palmitates, myristols, natural oils, and bees wax. Useful surfactants include, but are not limited to, anionic, cationic, and non-polar surfactants, as well as emulsifiers used in skin and/or scalp cleaning agents. Useful thickening agents include, but are not limited to, the natural gums.

The method of the invention comprises obtaining a composition comprising an active ingredient in an amount sufficient to inhibit the growth of *Propionibacterium acnes* in accordance with the invention, and topically applying the composition to skin for the treatment for acne. Preferably, the composition is applied from 1 to about 3 times a day.

DETAILED DESCRIPTION OF THE PREFERRED EMBODIMENTS

The present invention is directed to topical compositions for the treatment of acne, which are preferably non-irritating, and methods for treating acne by inhibiting the growth of *P. acnes* using an extract of at least one of grape seed, green tea, and cranberry. The grape seed and green tea extracts are preferably prepared as dried powders, while cranberry juice concentrate may be used without drying.

Green tea extract is preferably prepared from the leaves of *Camellia sinensis*. The tea leaves are collected and dried, and then cut, crushed, soaked, and extracted, preferably with a hydro-alcoholic solvent. The liquid extract is collected, and the alcohol is preferably removed under vacuum. A portion of the water may also be removed by vacuum. The extract may then be mixed with an appropriate carrier, and spray dried.

The cranberry extract is preferably prepared from the berries of *Vaccinium macrocarpon*. The whole berries are cold pressed to produce single strength juice. The juice is preferably then blended with an appropriate carrier, and spray dried.

Grape seed extract is preferably prepared from the seeds of *Vitis vinifera*. The seeds are collected and dried, and then soaked and extracted, preferably with an alcohol solvent. The liquid extract is collected, and the alcohol is preferably removed under vacuum until the residue is dry.

The extract is preferably applied in an appropriate carrier in an amount of from about 0.03 to about 1 percent based on the weight of the composition. The concentration may be varied, depending on whether the composition is left on the skin after application, or is removed, such as by rinsing or washing. Preferably, a composition of the invention is applied 1 to 3 times a day. As a result of the efficacy of the compositions of the invention, they may be substantially free of prior art acne treatments, such as copper lanolate, (5,4b)-isothiazolo pyridine-3-one, vitamin A, vitamin A derivatives, and amphiphilic lipid vesicles.

The compositions of the invention may also be used with prior art facial washes for deep cleansing, skin creams, lotions, sun screens, anti-aging creams and lotions, and moisturizers to add anti-acne benefits. In addition, the compositions of the invention may be used in combination with prior art acne treatments.

An in-vitro assay of the effectiveness of grape seed, cranberry, and green tea extracts as inhibitors of the growth of *P. acnes* was performed in a reinforced, clostridium medium, inoculated with *P. acnes*. In each assay, one of a 1,3-butylene glycol control and one or more extracts in 1 percent DMSO was added to the inoculated growth medium to provide samples having extract concentrations of 1, 0.5, 0.125, 0.063, 0.032, 0.016, and 0.008 percent.

Each of the extract solutions was prepared as follows. A dried, acetone extract in the form of a dry powder in an amount of 35 percent by weight was mixed with 35 percent 1,3-butylene glycol, and 30 percent water. A pressed, single-strength cranberry juice concentrate in an amount of 80 percent by weight, was mixed with 20 percent 1,3-butylene glycol. A dried alcohol/water extract of green tea leaf in an amount of 35 percent by weight was mixed with 35 percent 1,3-butylene glycol and 30 percent water.

Three mixtures containing grape seed extract were also tested. The grape seed/cranberry mixture contained 35 percent by weight of the dried grape seed extract, 50 percent of the cranberry juice concentrate, and 15 percent 1,3-butylene glycol. The grape seed/green tea extract mixture contained 25 percent by weight of each of the dried grape seed and green tea extracts, 20 percent 1,3-butylene glycol, and 30 percent water. The last mixture contained 25 percent by weight of each of the dried grape seed and green tea extracts, 20 percent of the cranberry juice concentrate, 10 percent 1,3-butylene glycol, and 20 percent water.

Following inoculation and the addition of 0.03 ml of a control or extract solution, each 3 ml sample was incubated for 2 days at 37° C. A turbidity measurement and a plating count of a subcultures was performed to determine the efficacy of each extract solution and the control.

The observed results were as follows. No inhibition was observed with the 1,3-butylene glycol control solution. Significant inhibition was observed in all samples containing with both the grape seed extract alone and the mixture of grape seed and green tea extracts. Therefore, the minimum concentration required for inhibition of *P. acnes* by both the grape seed extract alone and the mixture of grape seed and green tea extracts is no more than 0.032 percent by weight. Significant inhibition was observed in all samples of the mixture of grape seed extract and cranberry juice concentrate and the mixture of grape seed and green tea extracts with the cranberry juice concentrate at concentrations of at least 0.063 percent by weight. Therefore, the minimum concentration of those mixtures required for the inhibition of *P. acnes* is no more than 0.063 percent by weight. Substantial inhibition of *P. acnes* was observed in all samples of the green tea extract having a concentration of at least 0.125 percent by weight. Therefore, the minimum concentration of green tea extract required for the inhibition of *P. acnes* is no more than 0.125 percent by weight. For the cranberry juice concentrate, the observed minimum concentration required to inhibit *P. acnes* was 1 percent by weight.

Accordingly, it will be appreciated that the present invention has been described with references to particular preferred embodiments that are now contemplated. However, the invention is not limited by the embodiments disclosed herein and it will be appreciated that numerous modifications and other embodiments may be devised by those skilled in the art. Therefore, it is intended that the appended claims cover all such modifications and embodiments that fall within the true spirit and scope of the present invention.

What is claimed is:

1. A topical composition for the treatment of acne caused by *Propionibacterium acnes* consisting essentially of 25 percent by weight grape seed extract, 25 percent by weight green tea extract, 20 percent by weight 1,3-butylene glycol and 30 percent by weight water.

2. The topical composition of claim 1 wherein the grape seed extract and the green tea extract are dried extracts.

* * * * *